United States Patent
Leung et al.

(10) Patent No.: US 9,895,394 B2
(45) Date of Patent: Feb. 20, 2018

(54) INDUCTION OF CHRONIC ELEVATION OF INTRAOCULAR PRESSURE WITH VINYSULFONATED HYALURONIC ACID (HA-VS) AND THIOLATED HYALURONIC ACID (HA-SH)HYDROGEL

(71) Applicants: Kai-shun Christopher Leung, Hong Kong (CN); Ying Chau, Hong Kong (CN); Yu Yu, Hong Kong (CN)

(72) Inventors: Kai-shun Christopher Leung, Hong Kong (CN); Ying Chau, Hong Kong (CN); Yu Yu, Hong Kong (CN)

(*) Notice: Subject to any disclaimer, the term of this patent is extended or adjusted under 35 U.S.C. 154(b) by 0 days.

(21) Appl. No.: 14/643,757

(22) Filed: Mar. 10, 2015

(65) Prior Publication Data
US 2015/0250815 A1    Sep. 10, 2015

Related U.S. Application Data

(60) Provisional application No. 61/967,094, filed on Mar. 10, 2014.

(51) Int. Cl.
*A61K 31/738* (2006.01)
*A61K 49/00* (2006.01)

(52) U.S. Cl.
CPC ........ *A61K 31/738* (2013.01); *A61K 49/0008* (2013.01)

(58) Field of Classification Search
CPC .............. A61K 31/738; A61K 49/0008; A61K 9/0024; A61K 9/0048
See application file for complete search history.

(56) References Cited

U.S. PATENT DOCUMENTS

| | | | |
|---|---|---|---|
| 5,457,093 A * | 10/1995 | Cini | A61K 9/0014 514/21.2 |
| 2011/0200676 A1* | 8/2011 | Lin | A61K 9/0051 424/488 |
| 2012/0128741 A1* | 5/2012 | Gravett | A61L 27/26 424/400 |

FOREIGN PATENT DOCUMENTS

WO    WO 2012171335 A1 * 12/2012 ........... A61K 31/573

* cited by examiner

*Primary Examiner* — Titilayo Moloye
(74) *Attorney, Agent, or Firm* — Kilpatrick Townsend & Stockton LLP

(57) ABSTRACT

The present invention provides a method for inducing chronic elevation of intraocular pressure in the eyes of an animal by introducing into the eyes a cross-linking hydrogel, an animal produced by this method, as well as a screening method useful for identifying compounds capable of modulating intraocular pressure as well as for identifying compounds capable of modulating retinal ganglion cell survival and/or regeneration.

12 Claims, 5 Drawing Sheets

INDUCTION OF CHRONIC ELEVATION OF INTRAOCULAR PRESSURE WITH VINYSULFONATED HYALURONIC ACID (HA-VS) AND THIOLATED HYALURONIC ACID (HA-SH)HYDROGEL

RELATED APPLICATIONS

This application claims priority to U.S. Provisional Patent Application No. 61/967,094, filed on Mar. 10, 2014, the contents of which are incorporated by reference for all purposes in the entirety.

BACKGROUND OF THE INVENTION

Glaucoma is a blinding disease characterized by progressive degeneration of retinal ganglion cell and loss of visual function. While elevation of intraocular pressure (IOP) is a major risk factor for development and progression of glaucoma, the exact molecular and cellular mechanisms of glaucoma remain obscure[1]. All the available treatment options currently available for glaucoma patients aim to lower the IOP. Understanding the mechanisms and devising new treatment strategies to prevent blindness are unmet needs in glaucoma management.

Inducing IOP elevation in animal models is an important strategy for investigation of the mechanisms of retinal ganglion cell degeneration, and development and testing of new drugs and neuroprotective therapies for glaucoma. A number of experimental glaucoma models have been described in the literature. These include the transgenic DBA/2J mouse model[2-4], cauterization of episcleral vein[5-17], injection of hyertonic saline[18-22], laser photocoagulation of the trabecular meshwork[23-31], and intracameral injection of microbeads[32-38] and/or hyaluronic acid[39-40]. Although these models afford IOP elevation resulting in retinal ganglion cell degeneration, the longitudinal profile of IOP elevation in these models does not recapitulate to what researchers observe in glaucoma patients. Specifically, the IOP elevation is often transient, with high IOP spikes after induction of IOP elevation. Another side effect commonly encountered is development of cataract and corneal opacities, which would obscure in vivo examination of the optic nerve and retina. An ideal glaucoma model should demonstrate chronic (in terms of months, not weeks) and moderate elevation of IOP (high IOP elevation may result in retinal ischemia), with a clear optical media. Since these attributes are absent in the currently available glaucoma models, there exists a distinct need for developing new and better animal models for glaucoma research. The present invention fulfills this and other related needs.

BRIEF SUMMARY OF THE INVENTION

In one aspect, the present invention provides a method of inducing elevation of intraocular pressure in an eye of an animal. The method comprises the steps of: (1) injecting into the eye a solution comprising at least one crosslinkable polymer; and (2) permitting crosslinking of the polymer to form a cross-linked hydrogel in the eye, thereby elevating intraocular pressure (IOP) of the eye. The elevated IOP is to remain elevated for a length of time, e.g., days, weeks, or even as long as months.

In some embodiments, the polymer is a temperature responsive polymer or a pH responsive polymer. In some embodiments, the polymer is an ionic crosslinkable polymer or a chemically crosslinkable polymer, for example, the polymer maybe modified or functionalized with one or more of the following: acrylate, maleimide, vinylsulfone, N-hydroxysuccinimide, aldehyde, ketone, carbodiimide, carbonate, iodoacetyl, mercaptonicotinamide, quinone, thiol, and amine. In some cases, the solution may further comprise a cross-linker. In some embodiments, the polymer is hyaluronic acid, polyethylene glycol, dextran, carboxymethyl cellulose, polyvinyl alcohol, alginate, cyclodextran, or any combinations thereof. In some embodiments, the cross-linking is accelerated by a change in pH or temperature. In some cases, the solution prior to step (1) has a pH of 5-7.3 and a temperature of 2-34° C. In some embodiments, the solution further comprises a salt, an additional polymer, an organic solvent, or a therapeutic agent. In some embodiments, step (2) takes place in between 1 second to 10 minutes, for example, 30 seconds to 5 or 10 minutes, or 1 minute to 2, 3, 4, or 5 minutes. In some embodiments, the solution in step (1) is not viscous and has a viscosity of 1 cp to 1000 cp. In some embodiments, the method further comprises measuring intraocular pressure of the eye before step (1) and/or measuring intraocular pressure of the eye after step (2).

In a second aspect, the present invention provides an animal generated by following the herein described method of inducing elevated intraocular pressure. Such animals serve as highly valuable experimental models for studying glaucoma. An animal produced by the method described above typically retains the cross-linked hydrogel in the eye(s) that received the injection, and exhibits elevated intraocular pressure for a prolonged time period, e.g., from 10 days, up to 2-10 weeks, or 2, 3, 6, or 12 months. In some embodiments, the animal is a mammal, including a rodent, a rabbit or a primate, especially non-human primate such as a monkey or chimpanzee.

In a third aspect, the present invention provides a method for identifying compounds that can modulate intraocular pressure. The method comprises these steps: (1) administering a candidate compound to the animal generated by following the herein described method of inducing elevated intraocular pressure; (2) comparing test intraocular pressure, which is measured in the eye that has the cross-linked hydrogel in an animal that has been administered the candidate compound, with control intraocular pressure, which is measured in the eye has the cross-linked hydrogel in an animal that has not been administered the candidate compound; and (3) identifying the candidate compound as a modulator of intraocular pressure when the test intraocular pressure is higher or lower than the control intraocular pressure as determined in step (2). In some embodiments, the candidate compound is identified as an enhancer of intraocular pressure when the test intraocular pressure is higher than the control intraocular pressure. In other embodiments, the candidate compound is identified as a suppressor of intraocular pressure when the test intraocular pressure is lower than the control intraocular pressure. In some embodiments, the animal is a mammal, such as a rabbit, a rodent, or a non-human primate.

In a fourth aspect, the present invention provides a method for identifying a modulator of retinal ganglion cell survival and/or regeneration. The method comprises the steps of: (1) administering a candidate compound to the animal generated by following the herein described method of inducing elevated intraocular pressure; (2) comparing retinal ganglion cell density in the retina and/or axonal density in the optic nerve between a test eye that has the cross-linking hydrogel in an animal that has been administered the candidate compound and a control eye that has the cross-linking hydrogel in an animal that has not been administered the candidate compound; and (3) identifying the candidate compound as a modulator of retinal ganglion cell survival and/or regeneration when the test retinal ganglion cell density and/or axonal density is higher or lower than the control retinal ganglion cell density and/or axonal density as determined in step (2). In some embodiments, the candidate compound is identified as neuroprotective for retinal ganglion cells when the test retinal ganglion cell density and/or axonal density is higher than the control retinal ganglion cell density and/or axonal density. In some embodiments, the candidate compound is identified as neuroregenerative for retinal ganglion cells when the test retinal ganglion cell density and/or axonal density is higher after administration of the candidate compound compared with the test retinal ganglion cell density and/or axonal density before administration of the candidate compound. In some embodiments, the animal is a mammal, such as a rabbit, a rodent, or a non-human primate.

DETAILED DESCRIPTION OF THE INVENTION

I. Introduction

The present invention provides a novel method for inducing chronic and moderate elevation IOP elevation in an animal, including but not limited to rodents, rabbits, and other mammals such as non-human primates, by using an injectable hydrogel based material. An injectable formulation of hydrogel is prepared from a precursor polymer solution, i.e., a solution comprising at least one polymer that is capable of crosslinking to form a hydrogel. Once the hydrogel is injected into the eye of a recipient animal (e.g., the anterior chamber of the eye), the hydrogel transforms from a liquid to a solid gel. The gel obstructs the drainage of aqueous humor into the anterior chamber angle, resulting in elevation of IOP. The degree of IOP elevation can be titrated by varying the formulation of hydrogel and the volume of injection.

The present invention has the following advantages over the previously known similar methods: 1. The liquidity of the pre-polymerization hydrogel solution before injection enables its delivery into the anterior chamber even with a very fine glass needle or micropipette. 2. The transformation from a liquid to a solid state after injection prevent leakage upon injection into the anterior chamber. 3. Once polymerized, the hydrogel forms a three-dimensional network of nanoscale mesh that allows aqueous humor to diffuse into the gel, facilitating the delivery of nutrients to the cornea and the lens and thus preventing the development of cataract and corneal opacities. 4. The degree of IOP elevation can be adjusted by changing the crosslinking density (determined by the hydrophilic/hydrophobic ratio of the polymer) of the hydrogel as well as the volume of injection. 5. The hydrogel is transparent and does not obscure the optical media.

Figure 1:
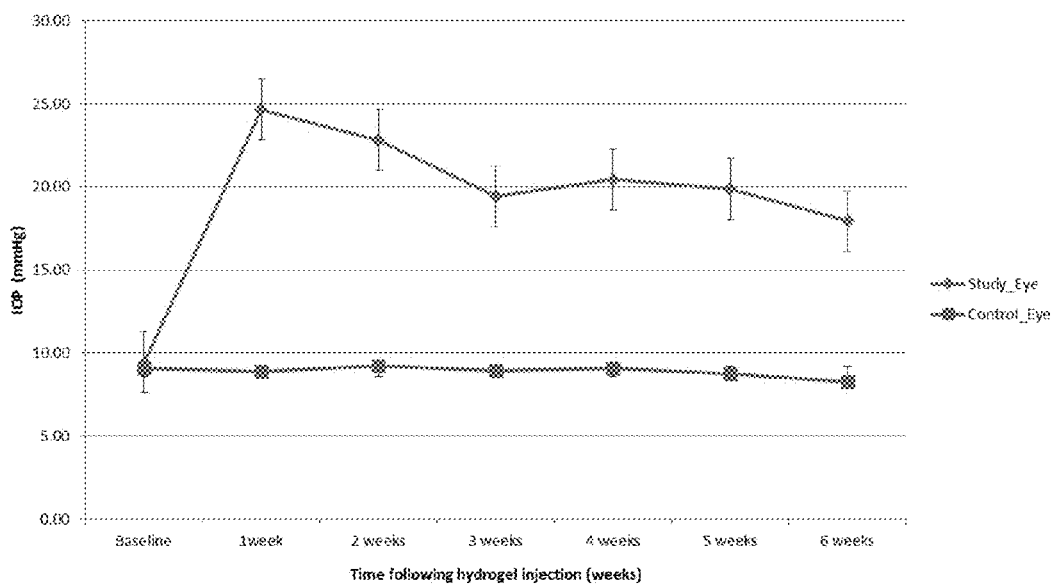
FIG. 1: Intraocular pressure (IOP) profiles of 8 mice with one eye injected with 1-2.5 μl of hydrogel (blue) and the fellow eyes as controls (red). This example demonstrates chronic, moderate elevation of IOP after injection of 1-2.5 μl of 4% vinysulfonated hyaluronic acid (HA-VS) and 4% thiolated hyaluronic acid (HA-SH) dissolved in phosphate buffered saline into the anterior chamber of eight C57/B6 mice. The injected eyes are indicated in blue and the fellow controls eyes are indicated in red (mean and standard error bars).
Figure 2:
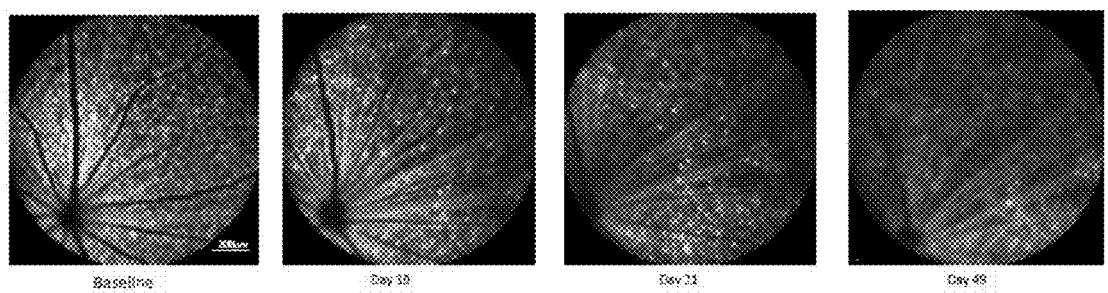
FIG. 2: in vivo imaging of retinal ganglion cells in a Thy-1 GFP transgenic mouse injected with 2.0 μl of hydrogel showing progressive and sectorial cell loss. In vivo longitudinal imaging of retinal ganglion cells is possible following the injection of hydrogel because the optical media remains clear. Progressive loss of retinal ganglion cells is noted.
Figure 3:
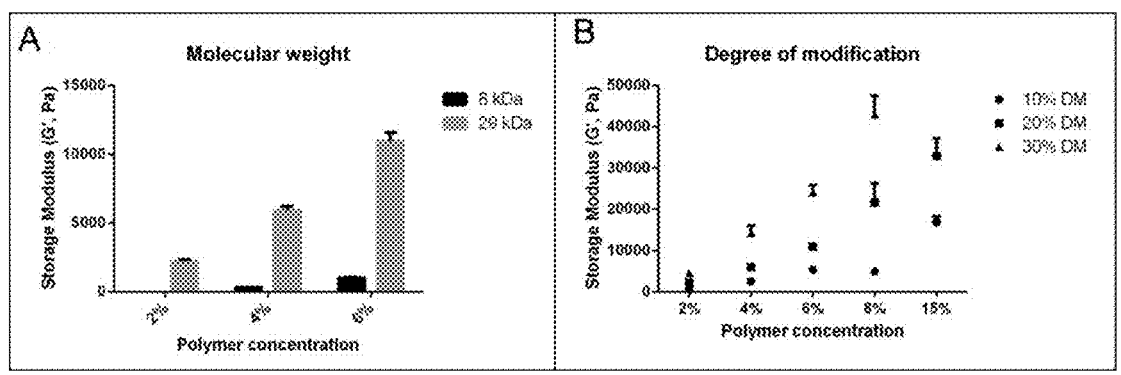
FIG. 3: Variation of storage modulus of different formulations of hydrogel composed of HA-VS and HA-SH with different polymer concentration and different molecular weight of HA (A) and different degree of modification (B). The degree of modification of the polymer in (A) was 20%. The molecular weight of the polymer in (B) was 29 kDa. All formulations were tested at room temperature (21° C.) and at pH 7.4. At least three replicas were tested for each formulation.
Figure 4:
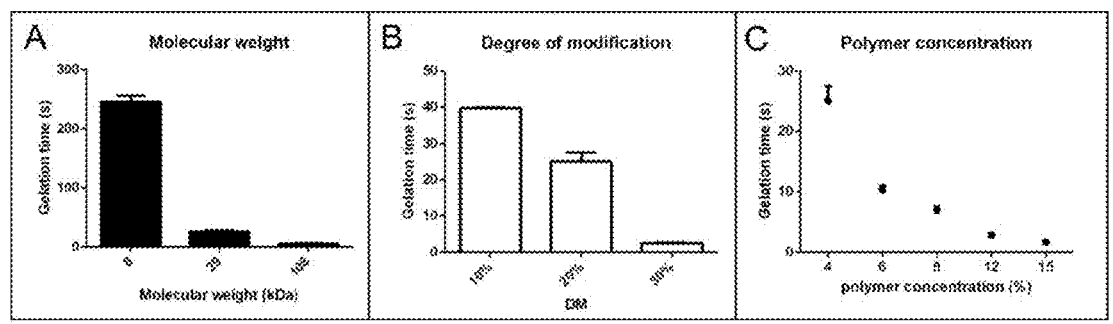
FIG. 4: Variation of gelation time of different formulations of hydrogel composed of HA-VS and HA-SH. The formulations can be modified by changing the molecular weight (A), the degree of modification (B) and the concentration (C) of the polymer. The degree of modification and concentration of the polymer in (A) was 20% and 4%, respectively. The molecular weight and concentration of the polymer in (B) was 29 kDa and 4%, respectively. The molecular weight and degree of modification of the polymer in (C) was 29 kDa and 20%, respectively. All formulations were tested at room temperature (21° C.) and at pH 7.4. At least three replicas were tested for each formulation. This figure shows that the gelation time can be controlled by varying the polymer formulations.
Figure 5:
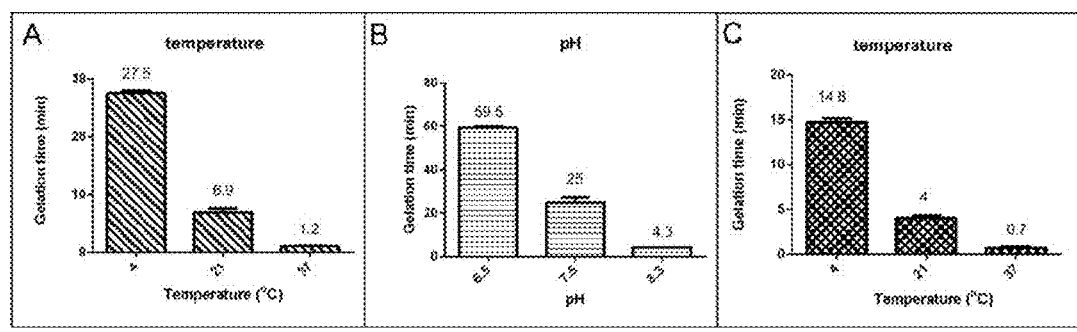
FIG. 5: Variation of gelation time with temperature and pH. The gel was composed of HA-VS and HA-SH. The molecular weight, concentration and degree of modification of the polymer were 29 kDa, 8% and 20%, respectively, in (A) and 29 kDa, 4% and 20%, respectively, in (B), and 29 kDa 6% and 20%, respectively, in (C). At least three replicas were tested for each formulation. This figure shows that the gelation time can be controlled by the environment of the polymer solution, e.g. temperature and pH. Specifically, the gelation time for HA-VS/HA-SH of various composition was decreased more than an order of magnitude when the temperature increase from 4° C. to 37° C. (close to the anterior chamber temperature, which is about 33 to 37° C. depending on the operating condition).

Development of neuroprotective and neurodegenerative therapies is an unmet need in the research of neurodegenerative diseases. This invention provides a unique approach to induce chronic degeneration of retinal neurons and facilitates in vivo monitoring of neurodegeneration and neuroregeneration. Animal models of experimental glaucoma are not only indispensable for glaucoma research but are also generally useful for research in neurodegenerative diseases. A new animal model with the advantages stated above will be recognized as a high-value tool for researchers in the pertinent field. To this end, the experimental data provided herein show that the method of this invention is effective in inducing intraocular pressure elevation (FIG. 1) with a clear optical media to monitor degeneration of retinal neurons (FIG. 2).

II. Hydrogel

A hydrogel is a cross-linked network or scaffolding of natural or synthetic polymer chains that are hydrophilic, sometimes found as a colloidal gel in which water is the dispersion medium. Being polymer networks that have high water-absorbing capacity, hydrogels often closely mimic native extracellular matrices. Although not water-soluble itself, a typical hydrogel also tends to possess a degree of flexibility very similar to natural tissues due to its relatively high water content: in some cases, hydrogels can contain over 90% water.

Common ingredients used in hydrogels include polyvinyl alcohol, sodium polyacrylate, acrylate polymers and copolymers with an abundance of hydrophilic groups. Natural hydrogel materials are being investigated for tissue engineering; these materials include agarose, methylcellulose, hyaluronic acid, and other naturally derived polymers.

Since hydrogels possess some natural tissue-like features, they are frequently used as biomaterials. As hydrogel-based cell delivery systems are being increasingly employed in regenerative medicine, several advances have been made in the hydrogel chemistry and modification for enhanced control of cell fate and functions, and modulation of cell and tissue responses against oxidative stress and inflammation in the tissue environment. The present inventors have provided a novel and unique method of inducing prolonged IOP elevation using hydrogels.

Briefly, the novel hydrogels of this invention comprise a water-filled cross-linked network polymers that can be classified as a viscoelastic solid (viscoelasticity is a phenomenon describing a mixed behavior of elasticity and viscosity of a material). Healon, Healon 5, and Healon GV (Abbott Medical Optics, Ill., USA) are examples of commercially available uncrosslinked polymer solutions or viscoelastic liquid. Although viscoelastic liquid has been used to induce IOP elevation in experimental glaucoma[39,40], the elevation is often transient and may not induce retinal ganglion cell degeneration. This is because the uncrosslinked nature facilitates the clearance of these material from the eye which causes a short and uncontrollable effect. However, if a polymer solution is cross-linked and forms a macroscopic gel, it is considered as viscoelastic solid. A solid material can provide persistent block to aqueous humor outflow at the anterior chamber angle, resulting in chronic elevation of IOP. The present inventors developed a hydrogel that can change from a viscoelastic liquid to a viscoelastic solid once the gel is injected into the anterior chamber of an eye. The pre-polymerization hydrogel material consists of one or more polymers capable of forming hydrogel gradually or instantly, depending on the formulation, and becomes a macroscopic hydrogel upon injection into the anterior chamber of the eye.

The material of hydrogel can be made of polymers that can undergo physical or chemical cross-linking after injection into the eye. Example of this type of polymer includes but not limited to a thermoresponsive polymer, a pH responsive polymer, a salt sensitive polymer, or a mixture of two or more polymers that can undergo chemical cross-linking after injection into the eye.

It should be noted that, additional components, for example, a viscosity modulating agent (e.g., a polymer), an organic solvent, a salt, a drug or imaging molecules, can also present in the solution of the gel precursor solution or conjugated to the gel precursor polymer and are not excluded in this disclosure.

The ability to form a macroscopic gel inside the eye within a reasonable time window is an important feature described by one or more of the embodiment. The hydrogel should be formed relatively fast after injection to prevent leakage from the injection site. However, the gelation process should not be too fast so that there is sufficient time for aspiration and injection.

One approach is to use a chemically crosslinkable material can control its gelation time to be within an injectable window. These hydrogel precursor polymers should be able to form chemical crosslink at physiological condition. The polymer solution is aspirated during this time window and injected to the eye. The hydrogel will be formed afterwards. This time window could be between 20 seconds to 2 hours. More preferably, the time window for gelation is between 2 minutes to 10 minutes. Examples of hydrogel precursors having such properties are polymers modified with a molecule selected from conjugated unsaturated groups including acrylate, maleimide, vinylsulfone, quinone, etc.; an active ester, including N-hydroxysuccinimide, an aldehyde, a ketone, a carbodiimide, a carbonate, an iodoacetyl, a mercaptonicotinamide, and combinations thereof. In some embodiments, at least one of the chemically crosslinkable agents is from polymers modified with a molecule selected from a nucleophile, such as, for example, a thiol and a amine. The gelation time of the crosslinkable polymer, is adjustable by changing the polymer composition including MW, concentration, DM and the type of polymer (different polymer backbone imposes different steric hindrance to the crosslinkable groups). The gelation time can be further fine-tuned by dissolving the polymer at an optimum pH and temperature. The gelation time can also be adjusted by changing the viscosity of the polymer solution. For example, alginate can be added into the polymer solution to increase the viscosity. Polymers including hyaluronic acid, dextran, polyethylene glycol, carboxymethyl cellulose, polyvinyl alcohol, alginate, cyclodextran can be modified to contain such crosslinkable groups. Preferably, the polymer is a polysaccharide.

Another approach is to use a "triggered gelation" material. This kind of material changes from a liquid to a solid gel within 3 minutes once the optimum gelation condition is provided. One example of triggered gelation is attained by changing the pH of the polymer solution. The cross-linking of the hydrogel polymerization slows down at a low pH. When the polymer solution is injected into the anterior chamber, the mixing of aqueous humor increases the pH in the anterior chamber and accelerates the gelation. Example of such gel could be physically crosslinked hydrogel and the polymer could be a polymer containing negatively charged or positively charged groups that has a pKa larger or smaller than 7.4 (physiological pH). These groups may be neutralized at physiological pH so that they are no longer charged and becomes hydrophobic. The hydrogels of this type are formed by hydrophobic interaction. Another example of such gel could be chemically crosslinked hydrogel having reactive groups that are optimally reacted at the pH closed to physiological pH of the animal. Examples of hydrogel precursors having such properties are polymers modified with a molecule selected from conjugated unsaturated groups including acrylate, maleimide, vinylsulfone, quinone, etc.; an active ester, including N-hydroxysuccinimide, an aldehyde, a ketone, a carbodiimide, a carbonate, an iodoacetyl, a mercaptonicotinamide, and combinations thereof. In some embodiments, at least one of the chemically crosslinkable agents is from polymers modified with a molecule selected from a nucleophile, such as, for example, a thiol and a amine. Preferably, the solution is not viscous before injection, for example, having a viscosity of 1 cp to 500 cp. To achieve such low viscosity, for hydrogel made from HA-VS and HA-SH, the molecular weight can thus be at the range of 5 kDa to 200 kDa, at the concentration of 1% w/v to 10% w/v. Another example of triggered gelation is by controlling the temperature. The cross-linking of the hydrogel precursor polymers is slowed down at a temperature that is different from the physiological temperature. When the polymer solution is being injected or after injected into the anterior chamber, the temperature of the polymer solution increases which accelerates the gelation. For instance, the polymers can be prepared at a temperature lower than 37° C., for example, at 4° C. to 33° C. During injection and after injection of the polymer, the temperature increase to about 20° C. to 40° C. Example of such gel could be temperature sensitively physically crosslinked hydrogel. Such hydrogel were made by polymeric materials for example poly(N-isopropylacrylamide) (PNIPAAm), poly(N,N-diethylacrylamide) (PDEAAm), poly(N-vinlycaprolactam) (PVCL), poly[2-(dimethylamino)ethyl methacrylate] (PDMAEMA), or block copolymers including ABA triblock copolymers of PNIPAAm (block A) and poly(N,N-dimethylacrylamide) (PDMAAm, block B). The hydrogels of this type are formed by hydrophobic interactions between temperature sensitive groups after the temperature changed to physiological temperature. Another example of such gel could be chemically crosslinked hydrogel having reactive groups that are highly reactive at physiological pH and temperature. Examples of hydrogel precursors having such properties are polymers modified with a molecule selected from conjugated unsaturated groups including acrylate, maleimide, vinylsulfone, quinone, etc.; an active ester, including N-hydroxysuccinimide, an aldehyde, a ketone, a carbodiimide, a carbonate, an iodoacetyl, a mercaptonicotinamide, and combinations thereof. In some embodiments, at least one of the chemically crosslinkable agents is from polymers modified with a molecule selected from a nucleophile, such as, for example, a thiol and a amine. Preferably, the solution is not viscous before injection, for example, having a viscosity of 1 cp to 500 cp. To achieve such low viscosity, for hydrogel made from HA-VS and HA-SH, the molecular weight can thus be at the range of 5 kDa to 200 kDa, at the concentration of 1% w/v to 10% w/v.

The gelation time of the triggered crosslinkable polymer, is fine turned by changing the polymer composition including MW, concentration, DM and the type of polymer (different polymer backbone imposes different steric hindrance to the crosslinkable groups). The gelation time can be further fine-tuned by dissolving the polymer at an optimum pH and temperature. Most desirably, such pH and temperature, in combination with the MW, concentration, DM and the type of the precursor polymer, result in a polymer solution that forms hydrogel slowly before injecting to the anterior chamber, but the gelation are significantly accelerated after injection. The gelation time for the polymer outside the eye can be in the range of 1 minute to 10 days. The gelation time after and during injection can be in the range of 1 second to 2 minutes. Most desirably, the gelation time for the polymer outside the eye can be in the range of 2.5 minutes to 10 days. The gelation time after and during injection to the anterior chamber can be in the range of 1 second to 1 minute.

Polymers including hyaluronic acid, dextran, polyethylene glycol, carboxymethyl cellulose, polyvinyl alcohol, alginate, cyclodextran can be modified to contain such crosslinkable groups. Preferably, the polymer is a polysaccharide.

Ideally, the gel being injected to the eye is transparent, elicit minimum allergic interaction with the animal's eye. More specifically, after the gel injection, the media of the eye is clear and in vivo imaging is possible. The animal could be a mouse, rabbit, rat, monkey, pig, dog, cat or any laboratory animals.

Since there is a large body of information in the pertinent field, some modifications can be adopted in order to achieve the desired features of a hydrogel for use in the present invention. For general reviews on hydrogels, see, e.g., Hennink and van Nostrum, *Adv Drug Deliv Rev.* 2002 January 17; 54(1):13-36; Ahmed, *Journal of Advanced Research* (2015) 6:105-121. For hydrogels that might be useful in the present invention see PCT/CN2012/000827 (published as WO2012/171335) and PCT/CN2012/001596 (published as WO2013/078770).

III. Generation of a New Glaucoma Animal Model

The present invention provides a method for generating an animal with elevated IOP, which is maintained for at least several days, to several weeks, to several months or even over 1 year. The level of elevation is at least 10%, 20%, 50%, 100%, or 200% over the average normal IOP of the animal.

The pre-polymerization hydrogel solution containing at least one monomer is injected into an animal's eye, e.g., into the anterior chamber, using established protocols commonly employed in the clinics. After sufficient time is passed and gelation is complete, IOP of the injected eye is typically measured and compared to the pre-injection IOP level to ensure that elevation at a desired level has been achieved. Further, post-injection IOP may be measured over the subsequent time periods such as days or weeks or just before the animal is to be used in studies to ensure proper IOP level is maintained.

Many species of animals may be suitable recipients of such injection for the purpose of elevating IOP. For example, any rodent species including rats or mice, other mammals such as rabbits, primates especially non-human primates such as monkeys or chimpanzees can be used. In some cases, humans may also receive such an injection in the event that elevated IOP is desired.

IV. Identification of Modulators of Intraocular Pressure and Modulators of Retinal Ganglion Cell Survival and Regeneration The animal model produced in accordance with the present invention is useful for identifying molecules and compounds that are potentially useful to modulate the intraocular pressure, as well as identifying molecules and compounds that are potentially capable of regulating or modulating the survival and regeneration of retinal ganglion cells independent of intraocular pressure. Generally, a candidate compound is administered to a test animal generated in accordance with the present invention. The administration may be systemic (e.g., via oral ingestion or via intravenous or intramuscular injection) or local (e.g., via local injection or via topical application to the eyes).

For identification of modulators of intraocular pressure, the intraocular pressure is measured in the test eye to yield test intraocular pressure values. In the meantime, the intraocular pressure in a control eye, which was generated by the same method but has not been administered the candidate compound, is measured to yield control intraocular pressure values. Upon comparing the test intraocular pressure values and the control intraocular pressure values, the candidate compound can be identified as an IOP modulator: it is determined as an IOP upregulator, i.e., a compound that increases intraocular pressure, when the test values are greater than the control values; or it is determined as an IOP suppressor, i.e., a compound that reduces intraocular pressure, when the test values are less than the control values.

For identification of modulators of retinal ganglion cell survival and regeneration, the survival and regeneration of retinal ganglion cells can be examined with counting of retinal ganglion cells in the retina and/or axonal fibers in the optic nerve with histological sections or in vivo imaging at multiple time points following administration of the modulators in the test eye and the control eye. Both the test and control eyes have elevated intraocular pressure induced by injection of cross-linking hydrogel into the anterior chamber. Upon comparing the density of retinal ganglion cells in the retina and axonal density in the optic nerve between a test eye and a control eye, the candidate compound can be identified to be neuroprotective to retinal ganglion cells when the densities of retinal ganglion cells and axons are higher in the test eye than the control eye. The candidate compound can be identified to be neuroregenerative to retinal ganglion cells and axons when the densities of retinal ganglion cells and axons are higher after administration of the candidate compound compared with the baseline.

Modulators of IOP and retinal ganglion cell survival and regeneration can have diverse chemical and structural features. For instance, a modulator could be a small molecule or macromolecule. Essentially any chemical compound can be tested as a potential modulator of IOP and retinal ganglion cell survival and regeneration. Most preferred are generally compounds that can be dissolved in aqueous or organic (especially DMSO-based) solutions. Modulators can be identified by screening a combinatorial library containing a large number of potentially effective compounds. Such combinatorial chemical libraries can be screened in one or more assays, as described herein, to identify those library members (particular chemical species or subclasses) that display a desired characteristic activity. The compounds thus identified can serve as conventional "lead compounds" or can themselves be used as potential or actual therapeutics.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)) and carbohydrate libraries (see, e.g., Liang et al., *Science*, 274:1520-1522 (1996) and U.S. Pat. No. 5,593,853). Other chemistries for generating chemical diversity libraries can also be used. Such chemistries include, but are not limited to: peptoids (PCT Publication No. WO 91/19735), encoded peptides (PCT Publication WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with P3-D-glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see, Sambrook and Russell, Molecular Cloning, A Laboratory Manual (3rd ed. 2001); Ausubel et al., eds., *Current Protocols in Molecular Biology* (1994)), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; and benzodiazepines, U.S. Pat. No. 5,288,514).

EXAMPLES

The following examples are provided by way of illustration only and not by way of limitation. Those of skill in the art will readily recognize a variety of non-critical parameters that could be changed or modified to yield essentially the same or similar results.

Example 1

Hyaluronic acid modified to contain vinylsulfone groups (HA-VS) of molecular weight (MW) 29 kDa, 20% degree of modification, 4% concentration in a phosphate buffered saline (PBS) is mixed with thiolated hyaluronic acid (HA-SH) of MW 29 kDa, 20% degree of modification, 4% concentration in PBS. The solution is injected to the anterior chamber of an animal. The IOP is elevated for a prolonged period of time after injection.

Example 2

HA-VS of MW 29 kDa, 20% degree of modification, 6% concentration in PBS is mixed with HA-SH of MW 29 kDa, 20% degree of modification, 6% concentration in PBS. The solution is injected to the anterior chamber. The IOP is elevated for a prolonged period of time after injection.

Example 3

HA-VS of MW 108 kDa, 20% degree of modification, 5% concentration in PBS is mixed with HA-SH of MW 108 kDa, 20% degree of modification, 5% concentration in PBS. The solution is injected to the anterior chamber. The IOP is elevated for a prolonged period of time after injection.

Example 4

HA-VS of MW 1.5 mDa, 20% degree of modification, 2% concentration in PBS is mixed with HA-SH of MW 108 kDa, 20% degree of modification, 4% concentration in PBS. The solution is injected to the anterior chamber. The IOP is elevated for a prolonged period of time after injection.

Example 5

HA-VS of MW 29 kDa, 20% degree of modification, 12% concentration in normal saline (pH 5.8) were mixed with HA-SH of MW 29 kDa, 20% degree of modification, 12% concentration in normal saline. The gelation is slow before injection and accelerates after injection into the anterior chamber with a pH of 7.4. The IOP is elevated for a prolonged period of time after injection.

Example 6

HA-VS of MW 29 kDa, 20% degree of modification, 10% concentration in normal saline (pH 5.8) is mixed with HA-SH of MW 29 kDa, 20% degree of modification, 10% concentration in normal saline. The solution is injected to the anterior chamber. The IOP is elevated for a prolonged period of time after injection.

Example 7

Alginate solution is injected into the anterior chamber and the polymer forms a physically crosslinked solid hydrogel when the salt in the aqueous humor is diffused into the polymer solution. Alternatively, calcium sulfate is added to the solution to increase the calcium concentration for increasing physical crosslink. The IOP is elevated for a prolonged period of time after injection into the anterior chamber.

Example 8

Dextran-VS of MW 40 kDa, 10% degree of modification, 6% concentration in PBS (pH 7.4) is mixed with dextran-SH of MW 40 kDa, 10% degree of modification, 6% concentration in PBS (pH 7.4). The solution is injected to the anterior chamber. The IOP is elevated for a prolonged period of time after injection.

Example 9

HA-VS of MW 29 kDa, 20% degree of modification, 6% concentration in BSS+ (~pH 8.5) is mixed with HA-SH of MW 29 kDa, 20% degree of modification, 6% concentration in BSS (~pH 7). The polymers were mixed on ice (~4° C.), and aspirated using a fine glass pipette when the polymer is cooled. The polymer is injected to the anterior chamber using the fine glass pipette. The gelation is slow before injection and accelerates after injection into the anterior chamber. The IOP is elevated for a prolonged period of time after injection.

Example 10

HA-VS of MW 29 kDa, 20% degree of modification, 6% concentration in BSS+(~pH 8.5) is mixed with HA-SH of MW 29 kDa, 20% degree of modification, 6% concentration in BSS (~pH 7). The polymers were mixed on ice (~4° C.), and aspirated using a syringe connected to a 30 gauge needle when the polymer is cooled. The polymer is injected to the anterior chamber using the 30 gauge needle. The gelation is slow before injection and accelerates after injection into the anterior chamber. The IOP is elevated for a prolonged period of time after injection.

Example 11

HA-VS of MW 29 kDa, 20% degree of modification, 6% concentration in BSS+(~pH 8.5) is mixed with HA-SH of MW 29 kDa, 20% degree of modification, 6% concentration in BSS (~pH 7). The polymers were mixed on ice (~4° C.), and aspirated using a syringe connected to a 30 gauge needle when the polymer is cooled. The polymer is injected to the anterior chamber using the 30 gauge needle. The gelation is slow before injection and accelerates after injection into the anterior chamber. The IOP is elevated for a prolonged period of time after injection.

Example 12

HA-VS of MW 29 kDa, 20% degree of modification, 10% concentration in PBS is mixed with HA-SH of MW 29 kDa, 20% degree of modification, 10% concentration in PBS. The polymers were mixed on ice (~4° C.), and aspirated using a syringe connected to a 30 gauge needle when the polymer is cooled. The polymer is injected to the vitreous chamber using the 30 gauge needle. The gelation is slow before injection and accelerates after injection into the anterior chamber. The IOP is elevated after injection.

Example 13

The gelation time for different polymer composition was measured by pipetting test. The two polymers were mixed at equal volume and the gelation time was determined when the gel is no longer aspiratable by a 10 ul pipette. For gelation at 4° C., a metal plate was place on ice in 4° C. refrigerator and polymers that were cooled on ice were mixed on the metal plate. For gelation at 37° C., the bottom of the metal plate was in contact with a 37° C. water bath and the polymers were warmed at the water bath before mixing. At least three replicas were conducted for each formulation.

Example 14

The storage modulus of the hydrogel was measured by dynamic mechanical analysis (DMA). Hydrogel of 8 mm (D)×1 mm (H) was placed on an 8 mm parallel plate fixture loaded to DMA machine (ARES Rheometer, TA Instruments, New Castle, Del.). G' was measured at 5 rad/s and 1% strain.

All patents, patent applications, and other publications, including GenBank Accession Numbers, cited in this application are incorporated by reference in the entirety for all purposes.

REFERENCES

1. Weinreb R N, Khaw P T. Primary open-angle glaucoma. Lancet. 2004; 363:1711-20.
2. Chang B, Smith R S, Hawes N L, et al. Interacting loci cause severe iris atrophy and glaucoma in DBA/2J mice. Nat Genet. 1999; 21:405-9.
3. Anderson M G, Smith R S, Hawes N L, et al. Mutations in genes encoding melanosomal proteins cause pigmentary glaucoma in DBA/2J mice. Nat Genet. 2002; 30:81-5.
4. John S W, Smith R S, Savinova O V, et al. Essential iris atrophy, pigment dispersion, and glaucoma in DBA/2J mice. Invest Ophthalmol Vis Sci. 1998; 39:951-62.
5. Urcola J H, Hernández M, Vecino E. Three experimental glaucoma models in rats: comparison of the effects of intraocular pressure elevation on retinal ganglion cell size and death. Exp Eye Res. 2006; 83:429-37.
6. Laquis S, Chaudhary P, Sharma S C, The patterns of retinal ganglion cell death in hypertensive eyes. Brain Res. 1998; 784:100-4.
7. Grozdanic S D, Betts D M, Sakaguchi D S et al. Temporary elevation of the intraocular pressure by cauterization of vortex and episcleral veins in rats causes functional deficits in the retina and optic nerve. Exp Eye Res. 2003; 77:27-33.
8. Garcia-Valenzuela E, Shareef S, Walsh J et al. Programmed cell death of retinal ganglion cells during experimental glaucoma. Exp Eye Res. 1995; 61:33-44.
9. Ahmed F A, Chaudhary P, Sharma S C. Effects of increased intraocular pressure on rat retinal ganglion cells. Int J Dev Neurosci. 2001; 19:209-18.
10. Naskar R, Wissing M, Thanos S. Detection of early neuron degeneration and accompanying microglial responses in the retina of a rat model of glaucoma. Invest Ophthalmol Vis Sci. 2002; 43:2962-8.
11. Sawada A, Neufeld A H. Confirmation of the rat model of chronic moderately elevated intraocular pressure. Exp Eye Res. 1999; 69:525-31.
12. Danias J, Shen F, Kavalarakis M et al. Characterization of retinal damage in the episcleral vein cauterization rat glaucoma model. Exp Eye Res. 2006; 82:219-28.
13. Mittag T W, Danias J, Pohorenec G et al. Retinal damage after 3 to 4 months of elevated intraocular pressure in a rat glaucoma model. Invest Ophthalmol Vis Sci. 2000; 41:3451-9.

14. Shareef S R, Garcia-Valenzuela E, Salierno A et al. Chronic ocular hypertension following episcleral venous occlusion in rats. Exp Eye Res. 1999; 61:379-82.
15. Ruiz-Ederra J, Verkman A S. Mouse model of sustained elevation in intraocular pressure produced by episcleral vein occlusion. Exp Eye Res. 2006; 82:879-84.
16. Villena A, Diaz F, Vidal L et al., Study of the effects of ocular hypotensive drugs on number of neurons in the retinal ganglion layer in a rat experimental glaucoma. Eur J Ophthalmol. 2009; 19:963-70.
17. Bayer A U, Danias J, Brodie S et al. Electroretinographic abnormalities in a rat glaucoma model with chronic elevated intraocular pressure. Exp Eye Res. 2001; 72:667-77.
18. Morrison J C, Moore C G, Deppmeier L M et al. A rat model of chronic pressure-induced optic nerve damage. Exp Eye Res. 1997; 64:85-96.
19. Johnson E C, Morrison J C, Farrell S et al. The effect of chronically elevated intraocular pressure on the rat optic nerve head extracellular matrix. Exp Eye Res. 1996; 62:663-74.
20. Chauhan B C, Pan J, Archibald M L et al., Effect of intraocular pressure on optic disc topography, electroretinography, and axonal loss in a chronic pressure-induced rat model of optic nerve damage. Invest Ophthalmol Vis Sci. 2002; 43:2969-76.
21. Jia L, Cepurna W O, Johnson E C et al. Patterns of intraocular pressure elevation after aqueous humor outflow obstruction in rats. Invest Ophthalmol Vis Sci. 2000; 41:1380-5.
22. Guo L, Moss S E, Alexander R A et al. Retinal ganglion cell apoptosis in glaucoma is related to intraocular pressure and IOP-induced effects on extracellular matrix. Invest Ophthalmol Vis Sci. 2005; 46:175-82.
23. Biermann J, van Oterendorp C, Stoykow C et al. Evaluation of intraocular pressure elevation in a modified laser-induced glaucoma rat model. Exp Eye Res. 2012; 104:7-14.
24. Aihara M, Lindsey J D, Weinreb R N. Experimental mouse ocular hypertension: establishment of the model. Invest Ophthalmol Vis Sci. 2003; 44:4314-20.
25. Mabuchi F, Aihara M, Mackey M R et al. Optic nerve damage in experimental mouse ocular hypertension. Invest Ophthalmol Vis Sci. 2003; 44:4321-30.
26. Levkovitch-Verbin H, Quigley H A, Martin K R et al. Translimbal laser photocoagulation to the trabecular meshwork as a model of glaucoma in rats. Invest Ophthalmol Vis Sci. 2002; 43:402-10.
27. Ji J, Chang P, Pennesi M E et al. Effects of elevated intraocular pressure on mouse retinal ganglion cells. Vision Res. 2005; 45:169-79.
28. WoldeMussie E, Ruiz G, Wijono M, et al. Neuroprotection of retinal ganglion cells by brimonidine in rats with laser-induced chronic ocular hypertension. Invest Ophthalmol Vis Sci. 2001; 42:2849-55.
29. Grozdanic S D, Betts D M, Sakaguchi D S et al. Laser-induced mouse model of chronic ocular hypertension. Invest Ophthalmol Vis Sci. 2003; 44:4337-46.
30. Gross R L, Ji J, Chang P et al. A mouse model of elevated intraocular pressure: retina and optic nerve findings. Trans Am Ophthalmol Soc. 2003; 101:163-9.
31. Ueda J, Sawaguchi S, Hanyu T et al. Experimental glaucoma model in the rat induced by laser trabecular photocoagulation after an intracameral injection of India ink. Jpn J Ophthalmol. 1998; 42:337-44.
32. Frankfort B J, Khan A K, Tse D Y et al. Elevated intraocular pressure causes inner retinal dysfunction before cell loss in a mouse model of experimental glaucoma. Invest Ophthalmol Vis Sci. 2013; 54:762-70.
33. Cone F E, Gelman S E, Son J L et al. Differential susceptibility to experimental glaucoma among 3 mouse strains using bead and viscoelastic injection. Exp Eye Res. 2010; 91:415-24.
34. Samsel P A, Kisiswa L, Erichsen J T et al. A novel method for the induction of experimental glaucoma using magnetic microspheres. Invest Ophthalmol Vis Sci. 2011; 52:1671-5.
35. Sappington R M, Carlson B J, Crish S D et al. The microbead occlusion model: a paradigm for induced ocular hypertension in rats and mice. Invest Ophthalmol Vis Sci. 2010; 51:207-16.
36. Chen H, Wei X, Cho K S et al. Optic neuropathy due to microbead-induced elevated intraocular pressure in the mouse. Invest Ophthalmol Vis Sci. 2011; 52:36-44.
37. Wei X, Yu Z, Cho K S et al. Neuroglobin is an endogenous neuroprotectant for retinal ganglion cells against glaucomatous damage. Am J Pathol. 2011; 179: 2788-97.
38. Yang Q, Cho K S, Chen H et al. Microbead-induced ocular hypertensive mouse model for screening and testing of aqueous production suppressants for glaucoma. Invest Ophthalmol Vis Sci. 2012; 53:3733-41.
39. Moreno M C, Marcos H J, Oscar Croxatto J et al. A new experimental model of glaucoma in rats through intracameral injections of hyaluronic acid. Exp Eye Res. 2005; 81:71-80.
40. Benozzi J, Nahum L P, Campanelli J L et al. Effect of hyaluronic acid on intraocular pressure in rats. Invest Ophthalmol Vis Sci. 2002; 43:2196-200.
41. Leung C K, Yu M, Weinreb R N, Lai G, Xu G, Lam D S. Retinal nerve fiber layer imaging with spectral-domain optical coherence tomography: patterns of retinal nerve fiber layer progression. Ophthalmology. 2012; 119(9): 1858-66.
42. Liu S, Li Z W, Weinreb R N, Xu G, Lindsey J D, Ye C, Yung W H, Pang C P, Lam D S, Leung C K. Tracking retinal microgliosis in models of retinal ganglion cell damage. Invest Ophthalmol Vis Sci. 2012; 53:6254-62.
43. Li Z W, Liu S, Weinreb R N, Lindsey J D, Yu M, Liu L, Ye C, Cui Q, Yung W H, Pang C P, Lam D S, Leung C K. Tracking dendritic shrinkage of retinal ganglion cells after acute elevation of intraocular pressure. Invest Ophthalmol Vis Sci. 2011; 52:7205-12.
44. Leung C K, Weinreb R N, Li Z W, Liu S, Lindsey J D, Choi N, Liu L, Cheung C Y, Ye C, Qiu K, Chen L J, Yung W H, Crowston J G, Pu M, So K F, Pang C P, Lam D S. Long-term in vivo imaging and measurement of dendritic shrinkage of retinal ganglion cells. Invest Ophthalmol Vis Sci. 2011; 52:1539-47.
45. Leung C K, Lindsey J D, Crowston J G, Lijia C, Chiang S, Weinreb R N. Longitudinal profile of retinal ganglion cell damage after optic nerve crush with blue-light confocal scanning laser ophthalmoscopy. Invest Ophthalmol Vis Sci. 2008; 49:4898-902.
46. W.-L. L. Suen and Y. Chau, "Size-dependent internalisation of folate-decorated nanoparticles via the pathways of clathrin and caveolae-mediated endocytosis in ARPE-19 cells," J. Pharm. Pharmacol., pp. 1-10, September 2013.
47. W.-L. L. Suen and Y. Chau, "Specific uptake of folate-decorated triamcinolone-encapsulating nanoparticles by retinal pigment epithelium cells enhances and prolongs antiangiogenic activity.," J. Control. Release, vol. 167, no. 1, pp. 21-8, April 2013.
48. W. Wang and Y. Chau, "Self-Assembly Mediated Platform for Rapid and Facile Preparation of Peptide-Functionalized Nanoparticles with High Stability," Chem. Mater., vol. 24, no. 5, pp. 946-953, March 2012
49. P. Zhou, Z. Li, and Y. Chau, "Synthesis, characterization, and in vivo evaluation of poly(ethylene oxide-co-glycidol)-platinate conjugate.," Eur. J. Pharm. Sci., vol. 41, no. 3-4, pp. 464-72, November 2010.
50. J. Zhong and Y. Chau, "Synthesis, characterization, and thermodynamic study of a polyvalent lytic peptide-polymer conjugate as novel anticancer agent.," Bioconjug. Chem., vol. 21, no. 11, pp. 2055-64, November 2010.
51. W.-L. L. Suen, H. S. Wong, Y. Yu, L. C. M. Lau, A. C.-Y. Lo, and Y. Chau, "Ultrasound-mediated transscleral delivery of macromolecules to the posterior segment of rabbit eye in vivo.," Invest. Ophthalmol. Vis. Sci., vol. 54, no. 6, pp. 4358-65, June 2013.
52. Y. Yu and Y. Chau, "One-step 'click' method for generating vinyl sulfone groups on hydroxyl-containing water-soluble polymers.," Biomacromolecules, vol. 13, no. 3, pp. 937-42, March 2012.
53. A. C. Y. Cheung, Y. Yu, D. Tay, H. S. Wong, R. Ellis-Behnke, and Y. Chau, "Ultrasound-enhanced intrascleral delivery of protein.," Int. J. Pharm., vol. 401, no. 1-2, pp. 16-24, November 2010.
54. Chau Y and Yu Y, Uses of Biocompatible in situ Gelling Agent, U.S. Provisional Patent Application (No. 61/629, 991)
55. Chau Y, Zhong J Y and Yu Y, Biocompatible in situ hydrogel, U.S. Provisional Patent Application (No. 61/854,108)

What is claimed is:

1. A method of elevating intraocular pressure in an eye of an animal, comprising the step of: (1) injecting into the eye a solution comprising vinysulfonated hyaluronic acid (HA-VS) and thiolated hyaluronic acid (HA-SH), wherein HA-VS and HA-SH have a molecular weight of 5 kDa to 200 kDa and a concentration of 1% to 10% w/v in the solution; (2) permitting crosslinking of hyaluronic acid to form a cross-linked hydrogel in the eye, thereby elevating intraocular pressure of the eye; and (3) measuring intraocular pressure of the injected eye, wherein the measured intraocular pressure of the injected eye is elevated by at least 10% when compared to the intraocular pressure of a non-injected control eye, and wherein the intraocular pressure of the injected eye remains elevated for at least 10 days after the crosslinking.

2. The method of claim 1, wherein the crosslinking is accelerated by a change in pH or temperature.

3. The method of claim 1, wherein the solution prior to step (1) has a pH of 5-7.3 and a temperature of 2-34° C.

4. The method of claim 1, wherein the solution further comprises a salt, an additional polymer, an organic solvent, or a therapeutic agent.

5. The method of claim 1, wherein step (2) takes place in between 1 second to 10 minutes.

6. The method of claim 1, wherein the solution in step (1) has a viscosity of 1 cp to 1000 cp.

7. The method of claim 1, further comprising measuring intraocular pressure of the eye before step (1).

8. An animal produced by the method of claim 1.

9. The animal of claim 8, wherein said animal is a mammal.

10. The mammal of claim 4, wherein said mammal is a rodent, a rabbit, or a non-human primate.

11. The method of claim 1, wherein in step (3) the measured intraocular pressure of the injected eye is elevated by at least 20% when compared to the intraocular pressure of a non-injected control eye.

12. The method of claim 1, wherein in the step (3) the measured intraocular pressure of the injected eye is elevated by at least 50% when compared to the intraocular pressure of a non-injected control eye.

* * * * *